United States Patent [19]

Siedel et al.

[11] Patent Number: 4,816,393

[45] Date of Patent: Mar. 28, 1989

[54] NUCLEOSIDE TRIPHOSPHATE-DEPENDENT 1-METHYLHYDANTOINASE, A PROCESS FOR OBTAINING IT AND THE USE THEREOF

[75] Inventors: Joachim Siedel; Rolf Deeg, both of Bernried; Albert Röder, Seeshaupt; Joachim Ziegenhorn, Starnberg; Hans Möllering; Helmgard Gauhl, both of Tutzing, all of Fed. Rep. of Germany

[73] Assignee: Boehringer Mannheim GmbH, Mannheim, Fed. Rep. of Germany

[21] Appl. No.: 704,712

[22] Filed: Feb. 25, 1985

[30] Foreign Application Priority Data

Feb. 24, 1984 [DE] Fed. Rep. of Germany ....... 3406770

[51] Int. Cl.$^4$ .......................... C12Q 1/34; C12Q 1/26; C12Q 1/32; C12N 9/14; C12N 9/86
[52] U.S. Cl. ........................................ 435/18; 435/25; 435/26; 435/195; 435/231; 435/810
[58] Field of Search ...................... 435/18, 25, 26, 28, 435/195, 231, 810, 814–816

[56] References Cited

U.S. PATENT DOCUMENTS

| | | | |
|---|---|---|---|
| 3,907,644 | 9/1975 | Möllering et al. | 435/18 |
| 4,087,329 | 5/1978 | Terada et al. | 435/18 |
| 4,134,793 | 1/1979 | Terada et al. | 195/103.5 R |
| 4,215,197 | 7/1980 | Tarbutton | 435/18 |
| 4,645,739 | 2/1987 | Deeg et al. | 435/25 |

FOREIGN PATENT DOCUMENTS

| | | | |
|---|---|---|---|
| 66552 | 12/1982 | European Pat. Off. | 435/18 |
| 3248145 | 6/1984 | Fed. Rep. of Germany | 435/18 |

OTHER PUBLICATIONS

Yamada et al, Chemical Abstracts, 104:105830q (1986), FEMS Microbiol. Lett., 30(3):337–340 (1985).

*Primary Examiner*—Esther M. Kepplinger
*Attorney, Agent, or Firm*—Felfe & Lynch

[57] ABSTRACT

The present invention provides 1-methylhydantoinase, which hydrolyses 1-methylhydantoin in the presence of a nucleoside triphosphate and of polyvalent metal ions.

The present invention also provides a process for obtaining 1-methylhydantoinase and a reagent containing it.

Furthermore, the present invention provides a process for the determination of creatinine by the conversion of the creatinine with creatinine deiminase (E.C. 3.5.4.21) into 1-methylhydantoin, hydrolysis of the latter with the 1-methylhydantoinase in the presence of nucleoside triphosphate and of polyvalent metal ions and determination (a) of the hydrolysis product formed from 1-methylhydantoin with N-carbamoylsarcosinamidohydrolase with formation of sarcosine and detection of the sarcosine with sarcosine oxidase or sarcosine dehydrogenase or (b) of the simultaneously formed nucleoside diphosphate.

24 Claims, 6 Drawing Sheets

NUCLEOSIDE TRIPHOSPHATE-DEPENDENT 1-METHYLHYDANTOINASE, A PROCESS FOR OBTAINING IT AND THE USE THEREOF

The present invention is concerned with a nucleoside triphosphate-dependent 1-methylhydantoinase, with a process for obtaining it and with the use thereof.

In analytical chemistry and especially in clinical-chemical diagnosis, there is a continuously increasing need for enzymatic processes for the determination of natural materials, biological metabolic products and compounds derived therefrom. The reasons for this are the extraordinarily high specificity of enzyme-catalyzed reactions, their rapid and stoichiometric course under mild reaction conditions (usually between 15° and 40° C. in an aqueous medium in the neutral pH range), as well as the possibility of quantitative detection in a simple and sensitive way, especially with photometric measurement methods, either directly or by coupled indicator reactions.

Hitherto, no enzyme-catalysed reaction process was known for 1-methylhydantoin which would have made this compound accessible to a direct or indirect enzymatic analysis. However, such a process would, inter alia, be especially valuable for the determination of creatinine, a clinically-diagnostically important serum and urine component which, in a longsince known enzyme reaction, can be converted by means of creatinine iminohydrolase (E.C. 3.5.4.21) into 1-methylhydantoin and ammonia.

For the enzymatic determination of creatinine in serum or urine, admittedly several processes are already known (A. W. Wahlefeld, G. Holz and H. U. Bergmeyer, in H. U. Bergmeyer: Methoden der enzymatischen Analyse, 3rd edition, Volume II publ. Verlag Chemie, Weinheim, 1974, pp. 1834–1838; P. Fossati, L. Prencipe and G. Berti, Clinical Chemistry, 29, 1494–1496/1983; and E. Tangenelli, L. Prenzipe, D. Bassi, S. Cambiaghi and E. Murador, Clinical Chemistry, 28, 1461–1464/1983). However, all these known processes have the disadvantage that they proceed either via creatine (Wahlefeld et al., Fossati et al.) or ammonia (Tanganelli et al.) as intermediate stages of the reaction sequence, i.e. substances which, ab initio, are present in the serum or urine samples to be analysed in varying concentrations which are clearly significant with regard to that of creatinine. Thus, for the determination of creatinine, differential measurements are necessary by two separate or successive reactions, in one of which the free creatine or ammonia is determined and in the second of which, by the addition either of creatinine amidohydrolase (E.C. 3.5.2.10) or creatinine iminohydrolase (creatinine deiminase), there is detected the amount of creatine or ammonia additionally formed from creatinine ("sample/sample blank process" or "$A_1/A_2$ process"). When such processes are carried out manually, they are relatively laborious and can be used in automated analysis systems only to a very limited extent, especially when, for the complete course of the reactions, comparatively long incubation times are necessary. Admittedly, in principle, by suitable choice of the reaction conditions, the creatinine determination can be carried out in the so-called kinetic "fixed time" process which avoids a sample blank measurement. However, this requires a very exact maintenance of the measurement interval under defined temperature conditions, which is possible with sufficient precision only in automatic analysers and which, on the other hand, substantially excludes a manual procedure.

Contrary to creatine or ammonia, 1-methylhydantoin (N-methylhydantoin, NMH) is not a natural component of serum or urine. Thus, a creatinine determination method proceeding via 1-methylhydantoin as intermediate product would offer the considerable advantage that a sample blank measurement can be omitted, provided the enzymatic conversion of 1-methylhydantoin can itself be used as in indicator reaction or possibly coupled indicator reactions also do not proceed via substances naturally occurring in the serum or urine in significant concentrations.

Therefore, there is a need for an agent and process for the enzymatic analysis of 1-methylhydantoin which makes possible its quantitative and preferably photometric determination without a simultaneous co-detection of other serum or urine components.

According to the present invention, this problem is solved by the discovery of a new and hitherto not known enzyme which is able to hydrolyse 1-methylhydantoin in the presence of at least one nucleoside triphosphate, preferably adenosine-5'-triphosphate (ATP), and of polyvalent metal ions, preferably $Mg^{2+}$ or $Mn^{2+}$, as well as possibly of an ammonium salt.

In the literature, there have admittedly already been described various enzymatic hydrolyses of hydantoins by "hydantoinases" (hydropyrimidine hydrolase, E.C. 3.5.2.2.) from various sources but hitherto it has only been possible to show an effectiveness towards unsubstituted hydantoin (D. P. Wallach and S. Grisolia, J. Biol. Chem., 226, 277–288/1957) or hydantoins substituted in 5-position (Federal Republic of Germany Patent Specification Nos. 26 31 048 and 28 11 303; R. Olivieri, E. Fascetti, L. Angelini and L. Degen, Biotechnology and Bioengineering, 23, 2173–2183/1981). Furthermore, a cofactor dependence has not been ascertained for any of the enzymes in question. The enzyme described by Wallach et al. also does not require, for example, the addition of polyvalent metal ions for the hydrolysis of hydantoin and Olivieri et al. even pointed to a clear inhibition of the hydantoin hydrolase in the presence of ammonium chloride (0.1 mol/liter), whereas the activity of the enzyme according to the present invention is considerably increased by the addition of ammonium salts.

The occurence, isolation and properties of the enzyme according to the present invention, as well as its use for the determination of 1-methylhydantoin or creatinine, are described in detail in the following.

The new enzyme 1-methylhydantoinase according to the present invention appears to occur widely in microorganisms. Thus, it has been discovered in microorganisms of the species Brevibacterium, Moraxella, Micrococcus and Arthrobacter. Examples of strains of these species, in which the enzyme of the present invention has been detected in amounts making its isolation worthwhile, include Arthrobacter spec. DSM 2563, DSM 2564, Moraxella spec. DSM 2562, Micrococcus spec. DSM 2565 and Brevibacterium spec. DSM 2843.

Therefore, the enzyme according to the present invention is preferably obtained by culturing one of the above-mentioned micro-organisms and isolating the enzyme from the biomass and/or from the culture medium.

The properties of the new enzyme are as follows:
I. Molecular weight
   (a) SDS gradient gel electrophoresis $M_r = 125,000$ II. pH optimum: pH=7.8 activity in %, 25° C.

| pH | 6.5 | 7.0 | 7.5 | 8.0 | 8.5 | 9.0 |
|---|---|---|---|---|---|---|
| TES buffer 150 mmol/liter | 5 | 76 | 100 | 100 | 95 | 69 |
| TRIS buffer 150 mmol/liter | 1 | 26 | 60 | 52 | 38 | 19 |

III. Specificity:
relative activity in % (via ADP/pyruvate kinase/lactate dehydrogenase)

(a) Substrate (0.1 mmol/l final concentration in the reaction mixture, each)

For the determination of the substrate specificity, the procedure is as follows:
1. Basic reagent

| component | concentration |
|---|---|
| potassium phosphate (pH 8.0) | 75 mmol/liter |
| NADH | 0.25 mmol/liter |
| ATP | 1.30 mmol/liter |
| phosphoenol pyruvate | 0.42 mmol/liter |
| MgCl₂ | 2.00 mmol/liter |
| pyruvate kinase | 4 U/ml. |
| lactate dehydrogenase | 10 U/ml. |

2. 1-Methylhydantoinase (15 U/ml. in 50% glycerol, 20 mmol/liter tris. HCl buffer, pH 8.0)
3. Hydantoin solutions
   Concentration of the hydantoins (1-methylhydantoin, hydantoin, 5-methylhydantoin, as well as 5,5-dimethylhydantoin): in each case 0.6 mmol/liter of water.
4. Assay procedure
   Wavelength 365 nm; T=25° C., d=1 cm.; test volume 1.21 ml. Pipette into cuvettes:

|  | sample | reaction mixture blank |
|---|---|---|
| basic reagent (1) | 1.00 ml. | 1.00 ml. |
| sample (3) | 0.20 ml. | — |
| water | | 0.20 ml. |
| mix, then add thereto | | |
| 1-methylhydantoinase (2) | 0.01 ml. | 0.01 ml. |
| measure ΔA of sample (ΔA$_p$) and of reaction mixture blank value (ΔA$_{RL}$) within 2 minutes after the addition of 1-methylhydantoinase ΔA = ΔA$_p$ − ΔA$_{RL}$ | | |

5. Calculation of the relative reaction velocity from the ΔA/min. determined with the various hydantoins (1-methylhydantoin=100%).
The following results were obtained:

1-methylhydantoin  100%

5-methylhydantoin  14 hydantoin  13

5,5-dimethylhydantoin  0

(b) Nucleotides

Relative activity in % (ATP=100) determined via the reaction sequence catalyzed by carbamoylsarcosinamidohydrolase+sarcosine oxidase:

| nucleotide (4 mmol/liter) | % |
|---|---|
| ATP | 100 |
| ADP | 1 |
| AMP | 0 |
| GTP | 7 |
| CTP | 1.5 |
| TTP | 0 |
| UTP | 0 |
| PPi | 0 |
| carb-phosphate | 0 |
| Na tripolyphosphate | 0 |
| Na hexametaphosphate | 0 |

4. Metalion dependence
Relative activity in % (5 mmol/liter magnesium chloride=100)

| mmol/liter | metal salt | % |
|---|---|---|
| 0 | MgCl₂ | 17 |
| 1 | " | 83 |
| 5 | " | 100 |
| 10 | " | 98 |
| 5 | MnCl₂ | 60 |
| 5 | ZnCl₂ | 24 |

5. Activators
Significant activation by NH₄⁺. Relative activity in % (30 mmol/liter ammonium sulphate (AS)=100)

| activator substance | mol/liter | % |
|---|---|---|
| none | 0 | 44 |
| (NH₄)₂SO₄ | 30 | 100 |
| (NH₄)₂SO₄ | 10 | 95 |
| NH₄Cl | 30 | 91 |
| NH₄ acetate | 30 | 98 |
| Li₂SO₄ | 30 | 40 |
| Na₂SO₄ | 30 | 39 |
| K₂SO₄ | 30 | 59 |
| NaCl | 30 | 41 |
| NaHCO₃ | 30 | 40 |

6. Inhibitors
Significant inhibition by EDTA, NaF. NaF: $1 \times 10^{-2}$ mol/liter leads to 100% inhibition EDTA in the presence of 7.5 mM Mg⁺⁺ in the reaction mixture:

| mol/liter | relative activity % |
|---|---|
| 0 | 100 |

-continued

| mol/liter | relative activity % |
|---|---|
| 5 | 100 |
| 10 | 42 |
| 50 | 2 |

7. Michaelis constants $K_m$ATP (TES 0.15 mol/liter, pH 7.8; via sarcosine)=0.8 mmol/liter; $K_m$ 1-methylhydantoin (0.15 mol/liter TES, pH 7.8; via ATP)=0.02 mmol/liter.
Stability
(a) temperature stability; in 50% glycerol; 20 mmol/liter Tris, pH 8.0 (2 U/ml.)

| 30 min. | residual activity in % |
|---|---|
| 25° C. | 100 |
| 50° C. | 94 |
| 60° C. | 70 |
| 70° C. | 0 |

(b) pH stability
20% glycerol, 10 mmol/liter Tris, 0.2 U/ml., +4° C., stored for 3 days in the dark (initial value=100%)

| pH | residual activity in % |
|---|---|
| 6.3 | 8 |
| 6.5 | 20 |
| 7.0 | 61 |
| 8.0 | 72 |
| 9.0 | 86 |

The enzyme according to the present invention can be obtained, by methods known for the purification of enzymes, from micro-organisms which contain a content of 1-methylhydantoinase making its isolation worthwhile. The micro-organism is preferably disintegrated and the enzyme precipitated by the addition of polyethyleneimine, an enzyme preparation thus being obtained which is already usable for analytical purposes. If a further purification is desired, it is preferable to use an ammonium sulphate fractionation, a heating step and also chromatography.

Disintegration of the micro-organism can be carried out by known chemical and physical methods, for example chemically by means of lysozyme or physically by ultrasonics, disruption in high pressure suspension and the like. Although the disintegration process is not critical, those methods which substantially break up the cell membrane are especially preferred.

The heat step expediently takes place at 50° C. in a pH range at which the enzyme displays a good stability.

For the chromatographic purification, phenylsepharose and DEAE group-containing, weakly basic anion exchangers have proved to be especially useful. A preferred purification process consists of a lysozyme digestion in 20% glycerol, precipitation by the addition of soluble polyethyleneimine, isolation of the precipitate, ammonium sulphate fractionation thereof, carrying out a heating treatment at 50° C. and pH 8 and chromatography on phenylsepharose, followed by chromatography on DEAE-"Sephacel" and subsequent molecular sieve fractionation, expediently over "Sephacryl". ("Sephacel" and "Sephacryl" are Registered Trade Marks). In this way, a pure enzyme preparation is obtained with a specific activity of 2.1 U/mg. protein which can be used to determine the properties of the enzyme.

The micro-organisms used for obtaining the enzyme are preferably cultivated on a nutrient medium which contains 1-methylhydantoin as a source of carbon and nitrogen, as well as vitamins and trace metals.

The present invention is also concerned with the use of 1-methylhydantoin for the determination of creatinine in aqueous, buffered solution by conversion of the creatinine with creatinine deiminase (E.C. 3.5.4.21) into 1-methylhydantoin, hydrolysis of the latter with the 1-methylhydantoinase in the presence of a nucleoside triphosphate, preferably present in excess, and of a polyvalent metal ion and determination.

(a) of the hydrolysis product formed from 1-methylhydantoin leading to the formation of sarcosine in the presence of N-carbamoylsarcosineamidohydrolase and detection of the sarcosine with either sarcosine oxidase or sarcosine dehydrogenase or (b) of the simultaneously formed nucleoside diphosphate.

Figure 2:
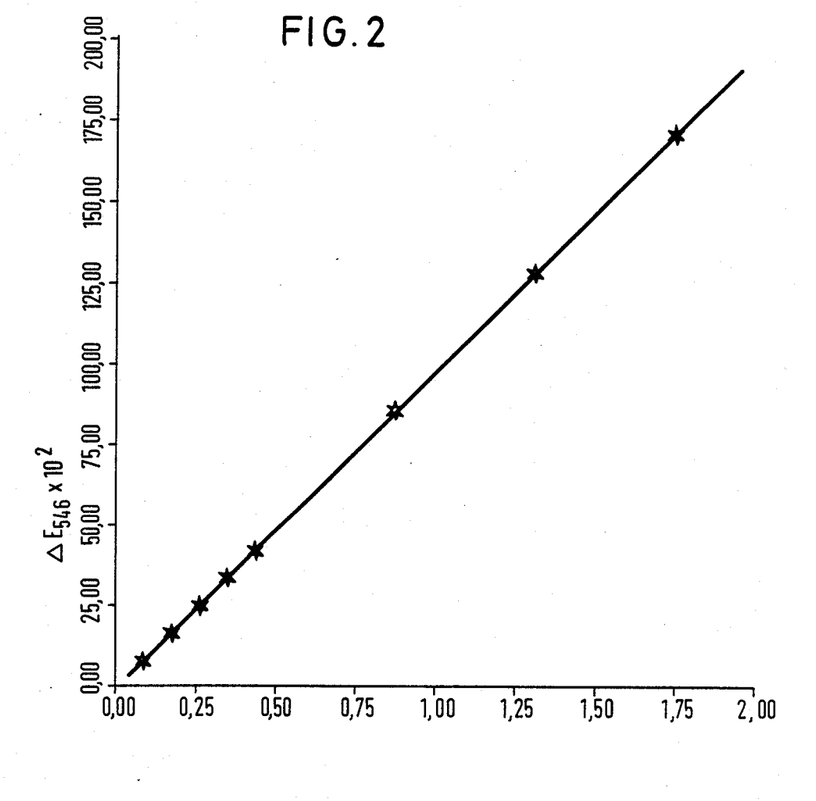
FIG. 2 is an illustration equivalent to FIG. 1 showing the use of N-carbamoylsarcosine instead of 1-methylhydantoin as in Example 6.
Figure 3:
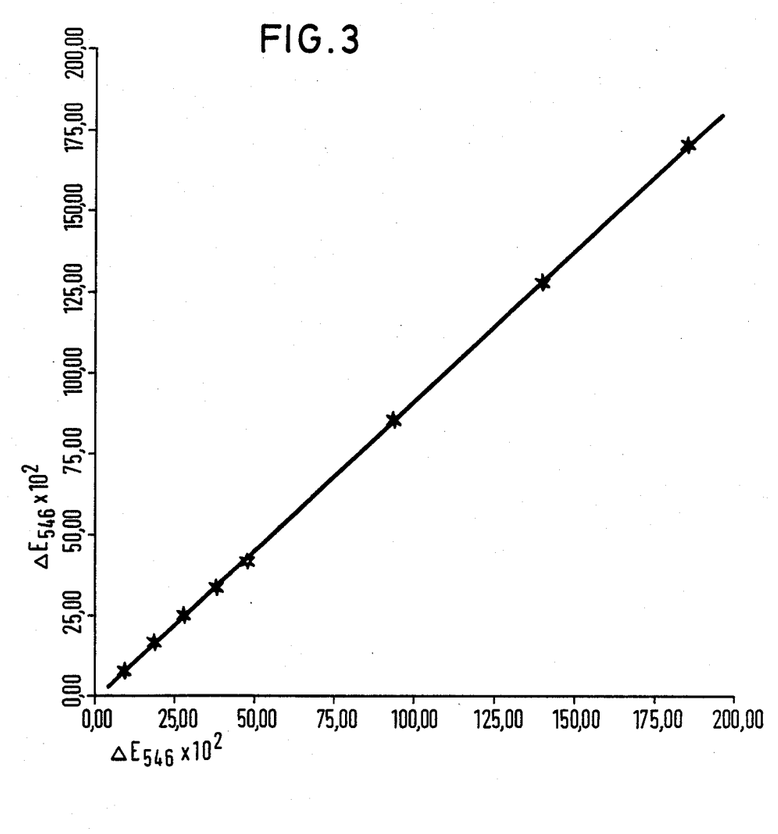
FIG. 3 is a graph comparing the results of Examples 5 and 6.

The 1-methylhydantoin hydrolysis product behaves, with regard to reaction velocity and measurement signal height, in the subsequent indicator reaction with N-carbamoylsarcosinamidohydrolase practically exactly as a reaction batch with, instead of 1-methylhydantoin, contains N-carbamoylsarcosine added in equimolar amount (see also FIGS. 2 and 3 of the accompanying drawings).

The pH value of the buffered aqueous solution is preferably from pH 7.0 to 9.0, more preferably from pH 7.3 to pH 8.5 and especially from pH 7.5 to pH 8.2. For the adjustment of the pH value, substances can be used which, in the mentioned pH range, display a sufficient buffer capacity, for example phosphate, Tris, triethanolamine or TES, TES buffer being especially preferred. Normally, the concentration of the buffer is from 10 to 500 mmol/liter, preferably from 50 to 200 mmol/liter and especially preferably from 75 to 125 mmol/liter.

As nucleoside triphosphate, there can be used ATP or GTP, ATP being preferred. The concentration range can thereby be from 0.05 to 50 mmol/liter, preferably from 0.5 to 20 mmol/liter and especially preferably from 1 to 10 mmol/liter.

The polyvalent metal ions used are preferably divalent metal ions, especially preferred being Mg and Mn ions and particularly Mg ions in the form of water-soluble salts, such as magnesium chloride or magnesium sulphate, as well as magnesium aspartate. The concentration of the metal ions can thereby be from 0.1 to 50 mmol/liter, preferably from 0.5 to 20 mmol/liter and especially preferably from 1 to 10 mmol/liter.

Per ml. of reaction mixture, there are normally used from 0.01 to 10 U 1-methylhydantoinase, preferably from 0.05 to 2 U and especially from 0.1 to 1 U.

For increasing the activity of the 1-methylhydantoinase, it has proved to be favourable to add ammonium salts, the concentrations thereof preferably being from 0.1 to 100 mmol/liter, more preferably from 1 to 30 mmol/liter and especially from 5 to 10 mmol/liter.

The creatinine iminohydrolase can be used in a concentration of from 0.1 to 20 U/ml., preferably of from 0.5 to 15 U/ml. and especially of from 1 to 10 U/ml.

For the N-carbamoylsarcosinamidohydrolase, activity concentrations of from 0.1 to 20 U/ml. are favourable, preferably from 0.5 to 10 U/ml. and especially from 1 to 5 U/ml. In addition, the statements in Federal Republic of German Paten Specification No. 32 48 145 apply analogously.

For the sarcosine oxidase, the favourable range is from 1 to 20 U/ml., preferably from 2 to 10 U/ml. and especially preferably from 4 to 8 U/ml. The same applies to the alternatively usable sarcosine dehydrogenase.

The detection of sarcosine with sarcosine oxidase or sarcosine dehydrogenase is known and the conditions known to the expert for this purpose can also be used according to the present invention. The same applies to the detection of the nucleoside diphosphate formed, i.e. of ADP or GDP. For this purpose, too, there can be used the known processes and reagents.

For the detection of the sarcosine formed, the use of the known sarcosine oxidase reaction is especially preferred. The course of the sarcosine oxidation can be monitored either electrochemically via the oxygen consumption or the hydrogen peroxide formation in the reaction medium or, preferably, enzymatically via the formation of hydrogen peroxide or formaldehyde. Particularly preferred is the determination of hydrogen peroxide by photometric methods, especially with a peroxidase-catalysed colour reaction by the oxidative coupling of 2,4,6-tribromo-3-hydroxybenzoic acid with 4-aminoantipyrine, the peroxidase activity thereby being from 0.05 to 20 U/ml., preferably from 0.2 to 10 U/ml. and especially from 0.5 to 5 U/ml. The tribromohydroxybenzoic acid is used in concentrations of from 1 to 25 mmol/liter, preferably of from 2 to 20 mmol/liter and especially of from 5 to 10 mmol/liter. In the case of 4-aminoantipyrine, it has proved favourable to use concentrations of from 0.1 to 2 mmol/liter, preferably of from 0.2 to 1.5 mmol/liter and especially of from 0.5 to 1 mmol/liter. Other known methods for the detection of hydrogen peroxide or, alternatively of formaldehyde can, however, also be used.

Since 1-methylhydantoinase stoichiometrically converts nucleoside triphosphate into nucleoside diphosphate, the creatinine determination can also be based, instead of on the determination of the reaction product formed from the 1-methylhydantoin, on the determination of the simultaneously formed nucleoside diphosphate, thus especially of ADP. Suitable processes for the determination of ADP are known, for example, from H. U. Bergmeyer "Methoden der enzymatischen Analyse", 3rd edition, 1974, page 2128 et seq. and 2178 et seq. Therefore, a detailed description is here unnecessary.

The present invention also provides a reagent for the determination of creatinine, which is characterised by a content of 1-methylhydantoinase.

Preferably, this reagent contains creatinine deiminase, 1-methylhydantoinase, ATP or GTP, divalent metal ions, N-carbamoylsarcosinamidohydrolase, sarcosine oxidase or sarcosine dehydrogenase and a buffer substance (pH 7.0 to 9.0)

The reagent preferably also contains a system for the determination of hydrogen peroxide or of formaldehyde or a colour-forming electron acceptor system, for example a tetrazolium salt, for the direct visualisation of the sarcosine dehydrogenase reaction. These systems are known, for example, from H. U. Bergmeyer, Methoden der enzymatischen Analyse, pub. Verlag Chemie, Weinheim.

Besides the mentioned components, the reaction mixture can also contain adjuvants, such as preserving agents, for example sodium azide, detergents and lipases for the clarification of samples that are turbid due to a high triglyceride content, as well as potassium ferrocyanide and ascorbate oxidase for the removal of disturbances from the hydrogen peroxide detection reaction brought about by the presence of bilirubin or ascorbic acid in the sample. For the use of the reaction mixture for the determination of 1-methylhydantoin alone, the creatinine iminohydrolase can also be omitted.

The reagents according to the present invention contain, as divalent metal ions, preferably magnesium or manganese ions, as already explained above in detail.

The mentioned reaction components can also be present impregnated on porous carrier materials and thereby make possible, for example, the quantitative or qualitative determination of creatinine or 1-methylhydantoin by means of so-called test strips.

In another preferred embodiment, the reagent according to the present invention contains creatinine deiminase, 1-methylhydantoinase, ATP or GTP, divalent metal ions, especially $Mg^{++}$ or $Mn^{++}$ ions, a system for the determination of ADP or GDP and a buffer substance (pH 7.0 to 9.0).

As buffer substance, in this case potassium phosphate buffer is preferred. For the concentrations of the buffer substance, creatinine deiminase, 1-methylhydantoinase, ATP, $Mg^{++}$ or $Mn^{++}$ ions, as well as possibly of ammonium salt, the statements made above apply analogously.

The ADP detection preferably takes please by use of a coupled pyruvate kinase/lactate dehydrogenase reaction in the presence of phosphoenol pyruvate and NADH, the amount of ADP formed thereby finally being detected photometrically via the NADH consumption in the lactate dehydrogenase reaction. This process is known and, therefore does not require further explanation here.

For the use of the reaction mixture for the determination of 1-methylhydantoin alone, the creatinine iminohydrolase can also be omitted.

The following examples are given for the purpose of illustrating the present inventiin, reference being made to the accompanying drawings, wherein.

The following abbreviations and synonyms are used:
AS: ammonium sulphate
carb-phosphate: carbamyl phosphate
CSHase: N-carbamoylsarcosinamidohydrolase
creatinine deiminase: creatinine iminohydrolase
1-methylhydantoinase, NMHase: 1-methylhydantoinhydrolase
N-methylhydantoin, NMH: 1-methylhydantoin
OD: optical density
PABA: p-aminobenzoic acid
PP: pyrophosphate
TES: 2-{[tris-(hydroxymethyl)-methyl]}- aminoethanesulphonic acid
TRIS: tris-(hydroxymethyl)-aminomethane.

EXAMPLE 1

(A) Culturing of the strain

Arthrobacter species DSM 2563 (isolated from soil) is maintained by subculture every three weeks on slant agar of the following composition:
per liter:

7 g. $Na_2HPO_4.2H_2O$; 3 g. $KH_2PO_4$; 0.5 g. NaCl; 0.5 g. $MgSO_4.7H_2O$; 10 g. N-methylhydantoin (NMH); 1 ml. trace solution 1+; 0.1 ml. trace solution 2++; 1 ml. vitamin solution +++; 20 g. agar; pH 7.5

+Trace solution 1:

100 mg. $MnCl_2.4H_2O$; 100 mg $FeCl_3.6H_2O$ and 100 mg. $CaCl_2.2H_2O$ dissolved in 100 ml. double distilled water and sterilised. 1 ml. of this solution per 1 liter of medium.

++Trace solution 2:

1 mg. $CuCl_2.2H_2O$; 1 mg. $ZnCl_2$; 1 mg. $(NH_4)_2MoO_4$ and 1 mg. $CoCl_2.6H_2O$ dissolved in 100 ml. double distilled water and sterilised. 0.1 ml of this solution per 1 liter of medium.

+++Vitamin solution:

0.1 mg. biotin; 0.1 mg. pyridoxol; 0.1 mg. pyridoxamine hydrochloride; 0.1 mg. PABA; 1.0 mg. riboflavin; 1.0 mg, nicotinamide; 1.0 mg. folic acid and 10.0 mg. thiamine hydrochloride dissolved in 100 ml. double distilled water and sterilised by filtration. 1 ml. of this solution per 1 liter of medium.

10 ml. of the above-described liquid medium are inoculated with 1 loopful of material from the slant agar culture and shaken in a 100 ml. Erlenmeyer flask for 20 to 24 hours at 28° C. Subsequently, these 10 ml. (first preculture) are transferred into 1000 ml. of the same medium and 200 ml. quantities thereof are further cultures in 1 liter Erlenmeyer flasks for 24 hours at 28° C. (OD 1:20=0.425). This second preculture is subsequently further inoculated at a concentration of 1% into 100 liters of the same medium in a fermenter and fermented for 18 hours at 28° C.

The maximum enzyme synthesis occurs at the end of the growth (late log phase). From the above-described batch are harvested 1180 g. of moist mass with 100 U/liter NMHase (1-methylhydantoinase) and 160 U/liter CSHase (N-carbamoylsarcosinaminohydrolase).

(B) Isolation and purification of the enzyme

From 280 g. of moist mass (=20 liters of culture) of Arthrobacter, there were isolated 500 U NMHase:

| step | vol. (ml.) | units | U/mg. protein | yield % |
|---|---|---|---|---|
| lysozyme digestion in 2% glycerol | 1400 | 1600 | 0.06 | 100 |
| polyethyleneimine precipitate | 430 | 1586 | — | 99 |
| ammonium sulphate fractionation = precipitate | 120 | 1181 | 0.40 | 73 |
| heating to 50° C. at pH 8 supernatant | 90 | 934 | 0.67 | 58 |
| phenyl-sepharose chromatography eluate after concentration | 60 | 830 | 1.20 | 52 |
| DEAE-Sephacel chromatography | 8 | 553 | 1.40 | 35 |
| molecular sieve fractionation Sephacryl S200 | 10 | 492 | 2.20 | 30.7 |

Final preparation:
data:
22.3 U/ml.
10.5 mg./ml.
2.1 U/mg. protein
50% glycerol
50 mmol/liter TRIS
pH=8.3

The activity determination was carried out as follows:

1. Colour reagent++:

| components | concentration |
|---|---|
| TES.KOH buffer (pH 7.8) | 162 mmol/liter |
| 4-aminoantipyrine | 0.81 mmol/liter |
| 2,4,6-tribromo-3-hydroxybenzoic acid | 8.1 mmol/liter |
| $MgCl_2$ | 8.1 mmol/liter |
| ATP | 4.3 mmol/liter |
| $(NH_4)_2SO_4$ | 32 mmol/liter |
| CSHase | 1.1 U/ml. |
| sarcosine oxidase | 6.5 U/ml. |
| peroxidase | 2.7 U/ml. |

2. 1-Methylhydantoin solution: 10 mmol/liter
3. Assay procedure:

Wavelength 546 mn; T=25° C.; light path 1 cm.; final volume 2.03 ml.; extinction coefficient of the dye formed=13 $cm^2/\mu mol$.

| pipette into cuvette | |
|---|---|
| colour reagent (1) | 1.88 ml. |
| sample+ | 0.05 ml. |
| mix, wait until sarcosine and N—carbamoylsarcosine possibly present in the sample have reacted, then start with | |
| 1-methylhydantoin (2) | 0.10 ml. |
| mix, monitor extinction increase and determine ΔA/min. from the linear range | |

+(sample material: For the determination of crude extracts, use supernatant of the high-speed centrifuged ultrasonic disintegration of the microorganisms in 20% glycerol, containing Tris.HCl (pH 8.0), 20 mmol/liter, as well as 0.1% Triton × 100.
++For the investigation according to Points 2, 3b, 4, 5 and 6 given hereinbefore in the description of the properties of the new enzyme, the corresponding substance concentrations or the nature of the added substances were alternatively altered.

4. Calculation:

$$U/ml. \text{ sample+} = \frac{\Delta A/min. \times 2.03}{13 \times 0.1} \text{ (if necessary} \times \text{ sample dilution)}$$

Remark: ΔA/min. must not to be more than 0.66; otherwise dilute sample. Lag phase about 5 minutes.

EXAMPLE 2

Moraxella spec. DSM 2562 (isolated from a cattle shed sample) is, as described in Example 1, kept on slant agar and cultured in the same medium as the Arthrobacter species.

Preculture 20 ml. NMH medium/100 ml. Erlenmeyer flask are inoculated from the slant agar culture and shaken for 21 hours at 28° C. (OD 1:20=0.430).

Main culture 8 ml. of the preculture are further inoculated into 400 ml. NMH medium in a 2 liter Erlenmeyer flask and cultivated, with shaking, for up to 43 hours at 28° C. In the biomass, disintegrated by means of ultrasonic treatment, the following activities were measured:

| hours cultivation | OD 1:20 | NMHase U/liter |
|---|---|---|
| 24 | 0.415 | 41 |
| 28 | 0.495 | 72 |
| 39 | 0.730 | 57 |

EXAMPLE 3

Brevibacterium species, DSM 2843 (isolated from a shed sample different from Example 2) is cultivated like Moraxella in Example 2.

Preculture:
21 hours at 28° C.; OD 1:20=0.690
Main culture:

| hours cultivation | OD 1:20 | NMHase U/liter |
|---|---|---|
| 15 | 0.440 | 26 |
| 24 | 0.550 | 80 |
| 39 | 0.670 | 59 |
| 43 | 0.750 | 46 |

EXAMPLE 4

Micrococcus spec. DSM 2565 (isolated from a soil sample) is cultivated like Moraxella in Example 2.

Preculture:
21 hours at 28° C.; OD 1:20=0.620
Main culture:

| hours cultivation | OD 1:20 | NMHase U/liter |
|---|---|---|
| 24 | 0.690 | 53 |
| 27.5 | 0.800 | 83 |

EXAMPLE 5

1. Enzymatic colour tetst for the determination of 1-methylhydantoin (1-methylhydantoinase/N-carbamoylsarcosinamidohydrolase/sarcosine oxidase reaction with peroxidase/4-aminoantipyrine/2,4,6-tribromo-3-hydroxybenzoic acid colour indicator system)

1.1. Reagent:

| components | concentration in the reagent |
|---|---|
| TES.KOH (pH 7.8) | 100 mmol/liter |
| MgCl$_2$ | 5 mmol/liter |
| ATP | 5 mmol/liter |
| NH$_4$Cl | 10 mmol/liter |
| 4-aminoantipyrine | 0.5 mmol/liter |
| 2,4,6-tribromo-3-hydroxybenzoic acid | 5 mmol/liter |
| 1-methylhydantoinase | 0.15 U/ml. |
| N—carbamoylsarcosinamidohydrolase | 2 U/ml. |
| sarcosine oxidase | 5 U/ml. |
| peroxidase | 2 U/ml. |

1.2 Assay procedure:
Wavelength: 546 nm
ligh path: 10 mm. Temperature: 25° C.
Measurement against reagent blank value pipette into cuvettes:

| | sample value (P) | reagent blank value (RL) |
|---|---|---|
| reagent 1.1 | 2.00 ml. | 2.00 ml. |
| sample+ | 0.10 ml. | — |
| water | — | 0.10 ml. | mix, incubate for 10 minutes and subsequently measure extinction of P against RL ($\Delta A$)

+aqueous solutions of 1-methylhydantoin, 87,7 to 1754 μmol/liter.

Figure 1:
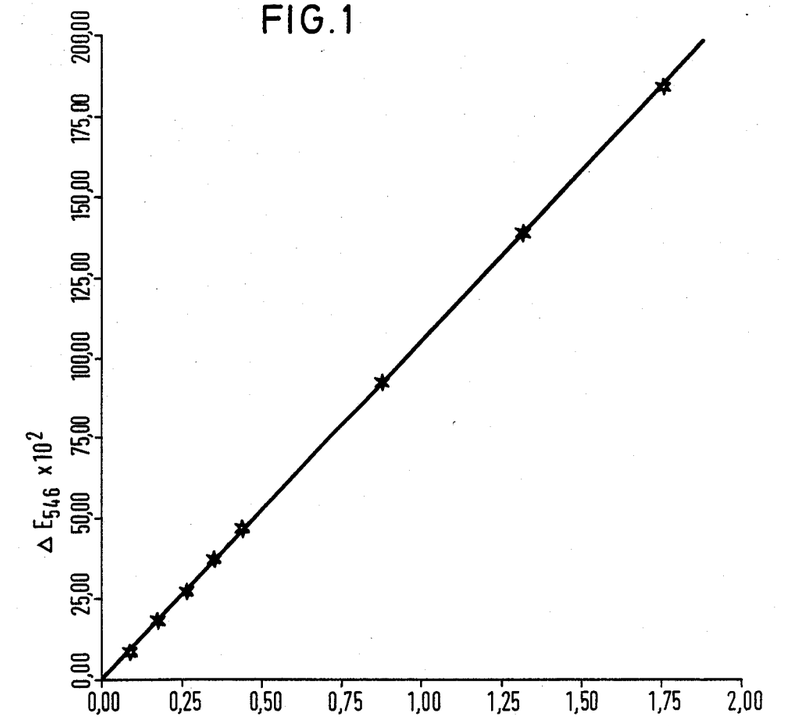
FIG. 1 is a graph illustrating the dependency of the absorbance values, obtained according to Example 5, on the amount of 1-methylhydantoin used.

The relation between $\Delta A$ and the particular concentration of 1-methylhydantoin in the sample used is given in FIG. 1 of the accompanying drawings.

EXAMPLE 6

Determination of N-carbamoylsarcosine with reagent 1.1 from Example 5

The determination is carred out analogously to Point 1.2 of Example 5 except that, instead of the aqueous 1-methylhydantoin solutions, there are used corresponding samples with equimolar concentrations (87.7 to 1754 mol/liter) of N-carbamoylsarcosine in the assay.

The dependency between the measured absorbance values and the concentration of N-carbamoylsarcosine is given in FIG. 2 of the accompanying drawings.

A comparison between the absorbance values measured according to Example 5 and 6 show that, with 1-methylhydantoin or N-carbamoylsarcosine samples, in each case at equimolar concentrations, identical colour signal heights are measured (see FIG. 3 of the accompanying drawings).

EXAMPLE 7

Enzymatic UV test for the determination of 1-methylhydantoin (1-methylhydantoinase/pyruvate kinase/lactate dehydrogenase reaction)

7.1. Reagents:
7.1.1. Reagent I:

| components | concentration in the reagent |
|---|---|
| potassium phosphate (pH 8.0) | 75 mmol/liter |
| NADH | 0.25 mmol/liter |
| ATP | 1.30 mmol/liter |
| phosphoenolpyruvate | 0.42 mmol/liter |
| MgCl$_2$ | 2.00 mmol/liter |
| pyruvate kinase | 4 U/ml. |
| lactate dehydrogenase | 10 U/ml. |

7.1.2. Reagent II:
1-Methylhydantoinase (15 U/ml. in 50% glycerol; pH 8.0)

7.2. Assay procedure:
Wavelength: 365 nm
Light path: 10 mm.
Temperature: 25° C.
Measurement against reagent mixture blank value
Pipette into cuvettes:

| | sample (P) | reaction mixture blank value (RL) |
|---|---|---|
| reagent I | 1.00 ml. | 1.00 ml. |
| sample++ | 0.20 ml. | — |
| water | — | 0.20 ml. | incubate 4 minutes, measure initial absorbance of sample ($A_{1,P}$) and of RL ($A_{1,RL}$). Then mix therewith:

| | | |
|---|---|---|
| NMHase | 0.01 ml. | 0.01 ml. |

After a further 5 to 10 minutes, measure absorbance

| | sample (P) | reaction mixture blank value (RL) |
|---|---|---|
| of P ($A_{2,p}$) and RL ($A_{2,RL}$). | | |
| $A = (A_{1,p} - A_{2,p}) - (A_{1,RL} - A_{2,RL})$+++ | | |

++aqueous 1-methylhydantoin solutions, 87.7 to 877 μmol/liter

+++If the 1-methylhydantoinase preparation still contains a significant amount of ATPase or NADH oxidase, which manifests itself in a enhanced NADH decrease in the reaction mixture blank value batch after addition of the 1-methylhydantoinase solution, $A_{2,p}$ and $A_{2,RL}$ must each be measured at precisely the same time after admixing of the NMHase, for example after 6.00 minutes.

Figure 4:
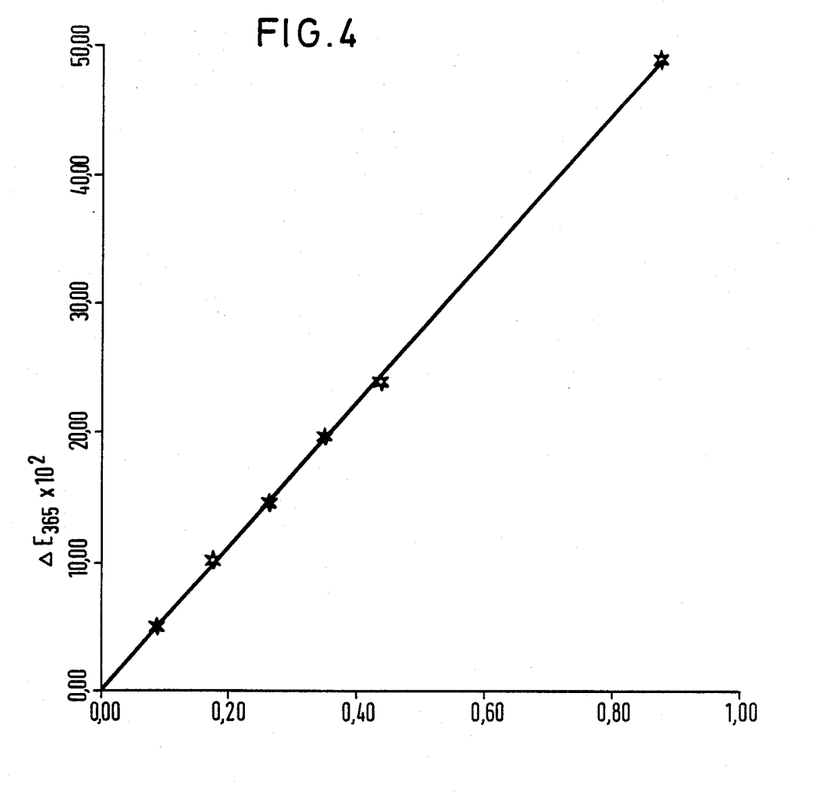
FIG. 4 is a graph equivalent to FIG. 1 for Example 7.
Figure 5:
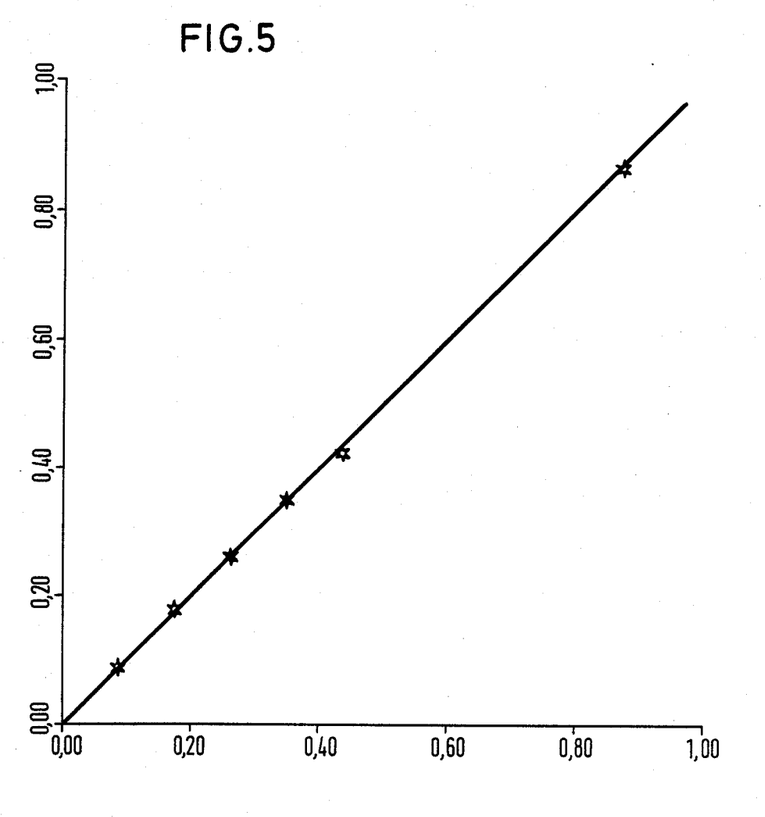
FIG. 5 is a graph illustrating the stoichiometric formation of ADP.

The dependency between the measured absorbance differences (ΔA) and the particular concentrations of 1-methylhydantoin in the sample is illustrated in FIG. 4 of the accompanying drawings. From the calculation of the amount of ADP resulting in the case of the hydrolysis of 1-methylhydantoin via the molar extinction coefficients of NADH at 365 nm, there is given a reaction stoichiometry of ATP consumption or ADP formation versus 1-methylhydantoin hydrolysis of 1:1 (see FIG. 5 of the accompanying drawings).

EXAMPLE 8

Enzymatic colour test for the determination of creatinine 8.1. Reagent:

Corresponding to reagent 1.1. of Example 5, however with the addition of creatinine iminohydrolase, 2 U/ml. (final concentration).

8.2. Assay procedure:

Corresponding to Point 1.2 of Example 5 but, as sample, there are used aqueous creatinine solutions (0.0877 to 1.754 mmol/liter) and the incubation period for P and RL is prolonged to 20 minutes.

Figure 6:
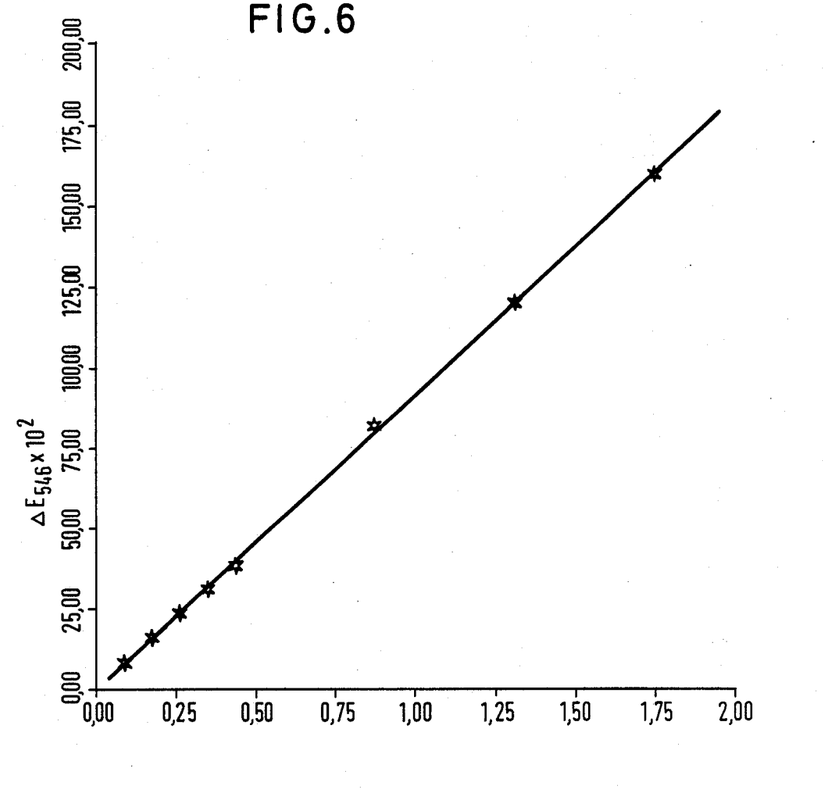
FIG. 6 is an illustration equivalent to FIG. 1 for Example 8.

The dependency of ΔA upon the concentration of creatinine in the sample is shown in FIG. 6 of the accompanying drawings.

If creatinine iminohydrolase is omitted from Reagent 8.1, then no colour reaction is observed, in the same way as when, in test batch 8.2, instead of the creatinine solutions, there is used a creatine solution (884 μmol/liter) as sample.

We claim:

1. Substantially pure 1-methylhydantoinase which hydrolyses 1-methylhydantoin in the presence of a nucleoside triphosphate and of polyvalent ions.

2. Process for the determination of creatinine comprising converting creatinine into 1-methylhydrantoin by action of creatinine deiminase, hydrolysing said 1-methylhydantoin with 1-methylhydantoinase in the presence of nucleoside triphosphate to form a 1-methyl-hydantoinhydrolysis product and a nucleoside diphosphate, and determining the nucleoside diphosphate as a determination of creatinine.

3. Process for obtaining the enzyme 1-methylhydantoinase comprising culturing Anthrobacter Spec. DSM 2563, or 2564; Moraxella Spec. DMS 2562; Micrococcus Spec. DSM 2565 or Brevibacterium Spec. DMS 2843 to produce said 1-methylhydantoinase and isolating the enzyme therefrom.

4. Process according to claim 3, wherein the microorganism is disintegrated, the enzyme is precipitated with polyethyleneimine and optionally further purified by ammonium sulphate fractionation, a heating step and chromatography.

5. The enzyme 1-methylhydantoinase obtained by the process of claim 3.

6. Process for the determination of creatinine comprising converting creatinine into 1-methylhydantoin by action of creatinine deiminase, hydrolyzing said 1-methylhydantoin with 1-methylhydantoinase in the presence of nucleoside triphophate and polyvalent metal ions to form a 1-methylhydantoin hydrolysis product, reacting said hydrolysis product with N-carbamoylsarcosineamidohydrolase to form sarcosine and determining the sarcosine with sarcosine oxidase or sarcosine dehydrogenase as a determination of creatinine.

7. Process according to claim 2 or 6, wherein the determination is carried out in a buffered aqueous solution at a pH value of from 7.0 to 9.0.

8. Process according to claim 2 or 6, wherein the determination is carried out in a buffered aqueous solution at a pH value of from 7.3 to 8.5.

9. Process according to claim 2 or 6, wherein the reaction is carried out at a buffer concentration of from 10 to 500 mmol/liter.

10. Process according to claim 2 or 6, wherein the reaction is carried out at a buffer concentration of from 50 to 200 mmol/liter.

11. Process according to claim 2 or 6, wherein said nucleoside triphosphate is adenosine triphosphate.

12. Process according to claim 11, wherein from 0.05 to 50 mmol/liter of ATP are used.

13. Process according to claim 2 or 6, wherein said polyvalent metal ions are magnesium or manganese ions.

14. Process according to claim 13, wherein said magnesium ions are in the form of magnesium chloride, magnesium sulphate or magensium aspartate.

15. Process according to claim 2 or 6, wherein said polyvalent metal ions are used in a concentration of from 0.1 to 50 mmol/liter.

16. Process according to claim 2 or 6, wherein said 1-methylhydantoinase is used in a concentration of from 0.01 to 10 U/ml.

17. Process according to claim 2 or 6, further comprising adding from 0.1 to 100 mmol/liter of an ammonium salt.

18. Process according to claim 6, wherein said N-carbamoylsarcosineamidohydrolase is added at a concentration of from 0.1 to 20 U/ml.

19. Process according to claim 18, further comprising adding from 1 to 20 U/ml sarcosine oxidase or sarcosine dehydrogenase.

20. Composition useful in the determination of creatinine comprising creatinine deiminase, 1-methyl hydantoinase, ATP or GTP, divalent metal ions, N-carbamoyl sarcosineamidohydrolase, one or sarcosine oxidase or sarcosine dehydrogenase and a buffer substance of a pH from 7.0 to 9.0.

21. Composition of claim 20, further comprising a system for determination of hydrogen peroxide or of formaldehyde, or a color-giving election acceptor system for direct visualization of the sarcosine dehydrogenase reaction.

22. Composition according to 20, further comprising Mg or Mn ions.

23. Composition useful in the determination of creatinine comprising creatinine deiminase, 1-methyl hydantoinase, ATP or GTP, divalent metal ions, a system for determination of ADP or GDP and a buffer of pH from 7.0 to 9.0.

24. Composition according to claim 23, wherein said system for determination of ADP comprises pyruvate kinase, lactate dehydrogenase, phosphoenol pyruvate, and NADH.

* * * * *